(12) United States Patent
Reigner et al.

(10) Patent No.: US 6,264,696 B1
(45) Date of Patent: Jul. 24, 2001

(54) TIBIAL KNEE PROSTHESIS COMPRISING A BALL JOINT WITH DOUBLE INSERTS

(75) Inventors: Bernard Reigner, Le Mans; Jean-François Biegun; Pascal Marceaux, both of Chaumont, all of (FR)

(73) Assignee: Aesculap (FR)

( * ) Notice: Subject to any disclaimer, the term of this patent is extended or adjusted under 35 U.S.C. 154(b) by 0 days.

(21) Appl. No.: 09/476,957

(22) Filed: Jan. 3, 2000

(30) Foreign Application Priority Data

Jan. 4, 1999 (FR) .................................................. 99 00012

(51) Int. Cl.[7] ...................................................... A61F 2/38
(52) U.S. Cl. ................... 623/20.24; 623/20.14; 623/20.26; 623/20.27
(58) Field of Search ............................... 623/20.24, 20.14, 623/20.26, 20.27, 20.21, 18.11, 16.11

(56) References Cited

U.S. PATENT DOCUMENTS

| | | | |
|---|---|---|---|
| 4,268,920 | 5/1981 | Engelbrecht et al. | 3/1.911 |
| 4,358,859 | * 11/1982 | Schurman et al. | 623/20.26 |
| 5,411,555 | * 5/1995 | Nieder | 623/20.24 |
| 5,766,257 | * 6/1998 | Goodman et al. | 623/20.14 |
| 5,800,552 | * 9/1998 | Forte | 623/20.27 |
| 5,824,102 | * 10/1998 | Buscayret | 623/20.21 |
| 5,954,770 | * 9/1999 | Schmotzer et al. | 623/20.24 |

FOREIGN PATENT DOCUMENTS

| | | | |
|---|---|---|---|
| 35 29 894 A1 | 3/1987 | (DE) | A61F/2/38 |
| 0 724 868 A1 | 8/1996 | (EP) | A61F/2/38 |

* cited by examiner

Primary Examiner—Pedro Philogene
(74) Attorney, Agent, or Firm—Renner, Kenner, Greive, Bobak, Taylor & Weber

(57) ABSTRACT

A knee endoprosthesis comprising: a tibial part comprising a tibial rod bearing a tibial plate, a first tibial insert (11) disposed on the tibial plate, a femoral part comprising a femoral rod bearing two condyles (8, 9) each having a first sliding surface co-operating and congruent with a respective second sliding surface formed on the first tibial insert (11), wherein the tibial part is coupled to the femoral part so that the femur can bend relative to the tibia from a position ($\alpha \approx 0$) where the knee is extended to a position ($\alpha_{max}$) where the knee is bent and vice versa. A progressive locking element is provided for limiting the lateral rotation and proper rotation of the condyles (8, 9) relative to the tibial plate, starting from a knee-bending angle $\alpha_0$ determined in advance and up to a zero angle, the amplitude of proper rotation, when the angle $\alpha_0$ is decreased, varying down to zero amplitude (complete blocking) at zero angle (unbent knee).

7 Claims, 4 Drawing Sheets

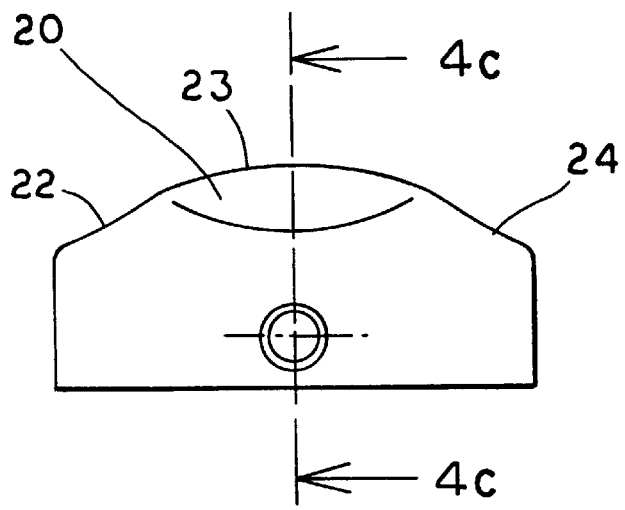
FIG.4b
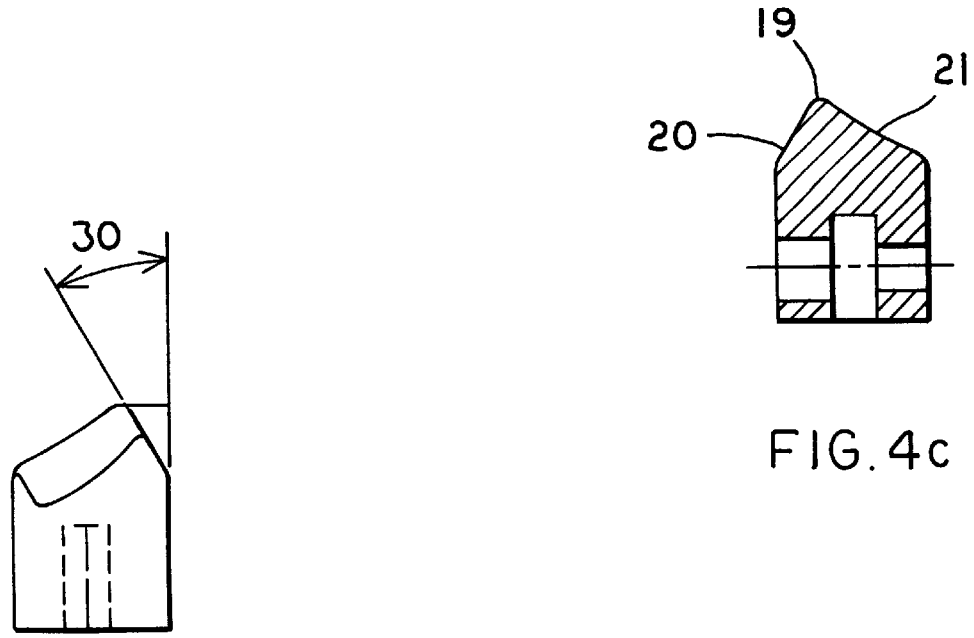
FIG.4c
FIG.4a

TIBIAL KNEE PROSTHESIS COMPRISING A BALL JOINT WITH DOUBLE INSERTS

TECHNICAL FIELD

The invention comprises a knee endoprosthesis of the kind comprising a tibial part comprising a tibial rod, one end of which is for inserting into the patient's tibia, and a tibial plate fixed to the other end of the tibial rod; a tibial insert disposed on the tibial plate; and a femoral part comprising a femoral rod and condyles borne by the femoral rod and each comprising a first sliding surface corresponding in shape to a second sliding surface on the tibial insert, the condyles being at least partly separated by an intercondylar space;

the condyles and the tibial insert co-operating via a coupling means such as a journal which extends through the tibial insert via an opening formed in the insert and is fixed to the tibial part; and a coupling head extending into the intercondylar space and a coupling shaft fixed to the condyles and extending into an opening in the coupling head, so that the femoral part can pivot relative to the coupling shaft and thus move from an unbent position (total extension of the knee) to a bent position (approximately 120° bend of the knee).

A knee prosthesis of this kind is known e.g. from the document EP-0 791 343.

Knee prostheses of this kind have a number of disadvantages.

BACKGROUND OF THE INVENTION

The tibial insert, usually of polyethylene, is mounted so as to be freely rotatable relative to the tibial plate (generally of metal) so as to permit clearance in proper rotation of the femur relative to the tibia, the proper rotation occurring via the condyles (usually of metal) which slide on the corresponding sliding surfaces of the tibial insert. In the unbent position (knee bending angle $\alpha=0°$) of the knee, rotation of the femur relative to the tibia is blocked by the condyles abutting on the polyethylene insert. As soon as the knee bends, however, ($\alpha$ becomes greater than 0) the block is completely relaxed and the femur can rotate over a very wide angle before the knee has appreciably bent. This is not a true reproduction of the anatomical knee and may result in undesirable jamming.

SUMMARY OF THE INVENTION

The invention aims to obviate these disadvantages by providing a prosthesis in which, when the knee moves from a completely unbent position, the femur part is locked to the tibial part progressively during extension (unbending) of the knee.

This is achieved by providing a progressive locking element adapted to limit the proper rotation of the condyles relative to the tibial plate, starting from a knee-bending angle $\alpha_0$ determined in advance and up to a zero angle, the amplitude of proper rotation decreasing from the angle $\alpha_0$ to zero amplitude (total locking) at a zero angle (unbent knee).

According to an advantageous improvement of the invention, the progressive locking element comprises a second tibial insert fixed to the tibial plate and having a shape such that when the knee is in the extended position the second fixed tibial insert projects into an intercondylar space formed between the condyles and fits into the seat formed by the intercondylar space so as to block any axial rotation of the femur relative to the tibia, and such that when the knee bends and the second insert comes out of its seat, a clearance between the walls of the intercondylar space and the second insert occurs progressively up to a bending angle ($\alpha_0$) determined in advance, after which the movements in axial rotation are free.

This special arrangement prevents the rotary tibial insert from being used for progressively blocking the condyles and thus wearing out as quickly as in the case where the blocking element is an integral part of the tibial insert, in which case the tibial insert, which can rotate freely relative to the tibial plate, will be stressed both by bending and by axial rotation or in varus/valgus. In the present case, the movable insert is stressed only during bending, since the stresses during axial rotation or in valus/valgus, inter alia in the locked position, are borne entirely by the fixed second tibial insert.

In an improvement according to the invention, the coupling means is fixed relative to the tibial plate in order still further to limit the possibility of proper rotation and thus additionally lock the femur when in the unbent position relative to the tibia.

BRIEF DESCRIPTION OF THE DRAWINGS

FIGS. 4a, 4b and 4c, are views from the side, the front and in section 4c—4c respectively, of the fixed insert.

DETAILED DESCRIPTION OF THE INVENTION

Figure 1:
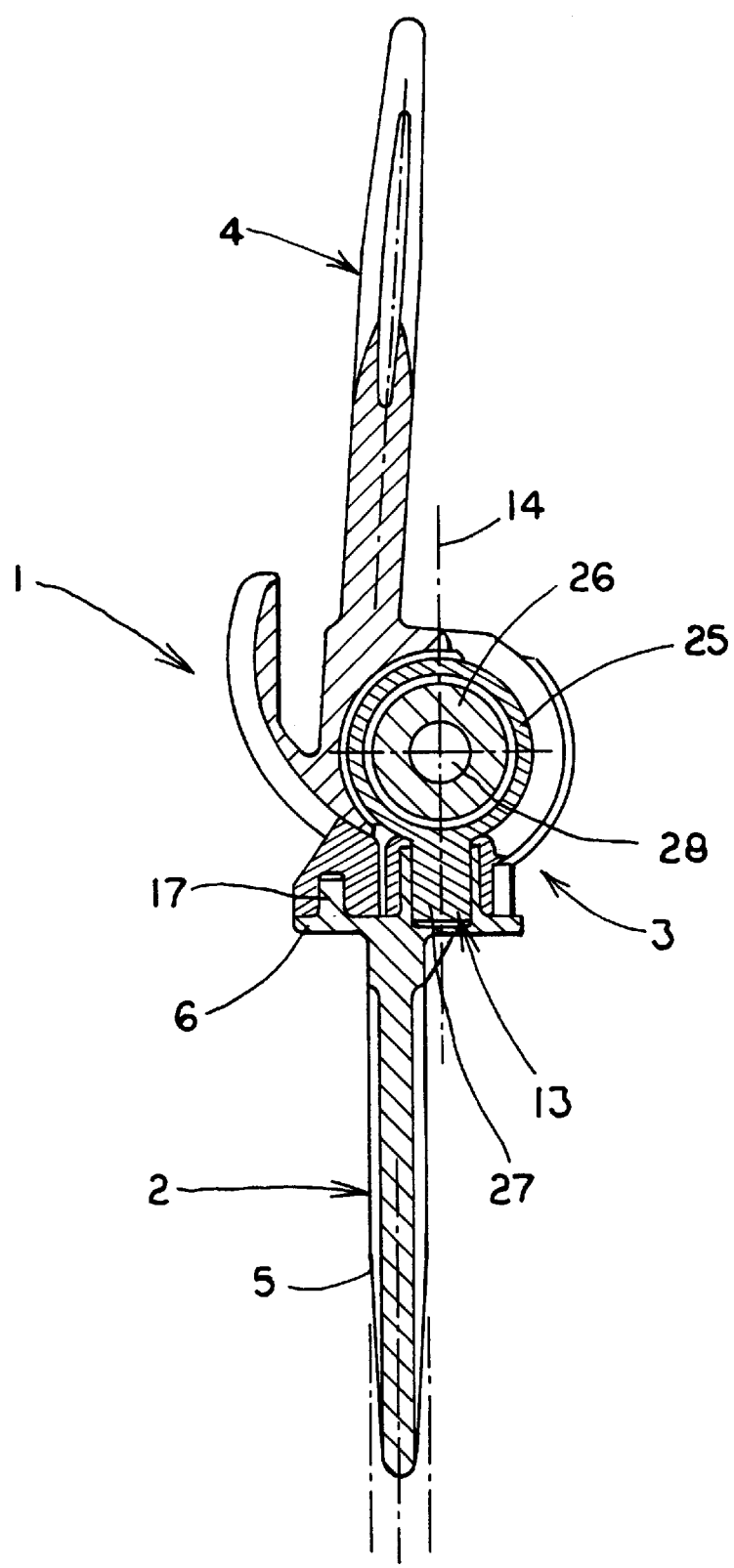
FIG. 1 is a view in lateral section of a knee prosthesis according to the invention, in the unbent position.
Figure 2:
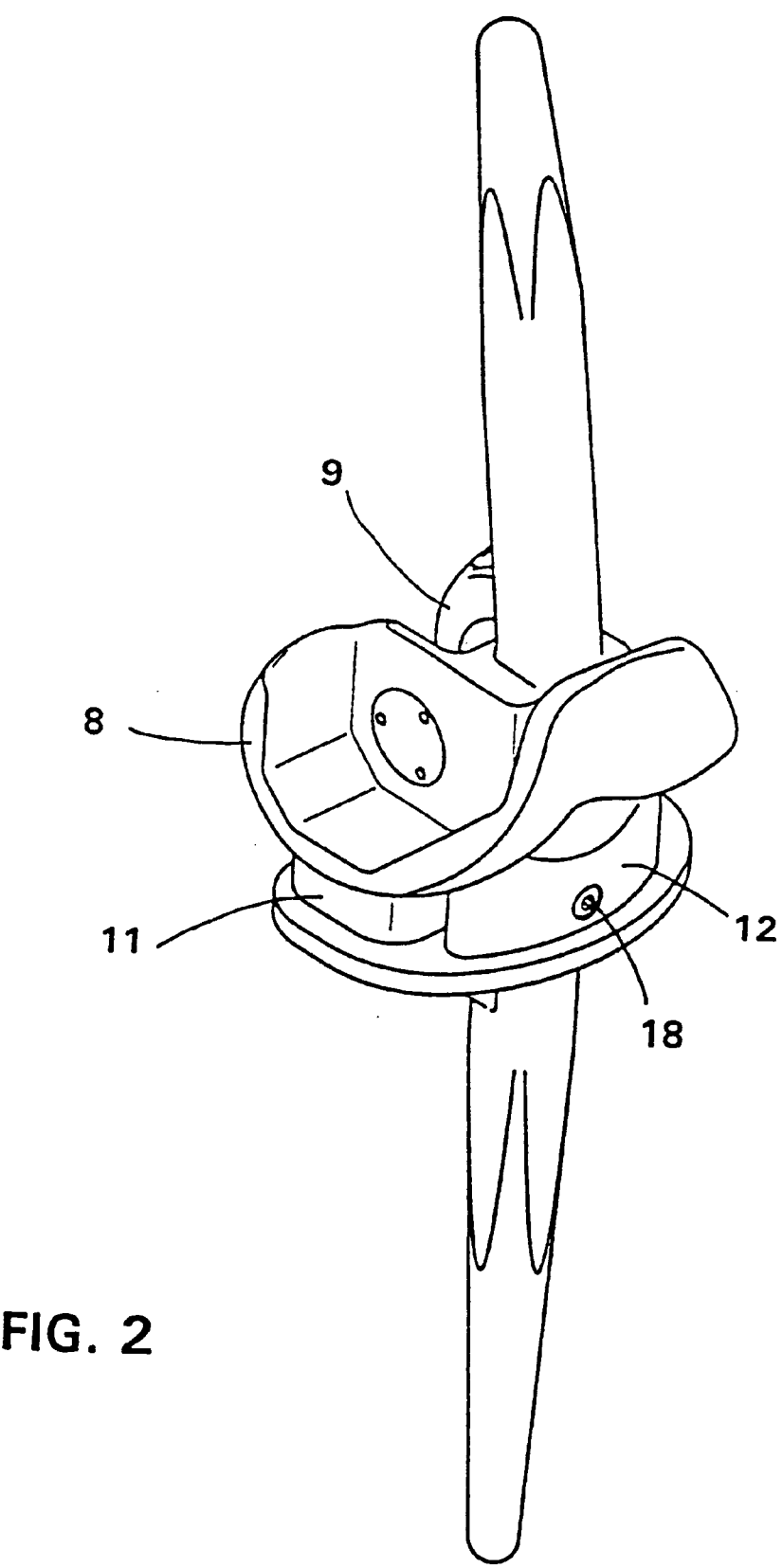
FIG. 2 is a perspective view of the prosthesis in FIG. 1, also in the unbent position.

FIG. 1 shows a knee prosthesis 1 comprising a tibial part 2, a coupling part 3 and a femoral part 4.

The tibial part 2 comprises a tibial rod 5 for inserting and fixing in the medullary canal of the tibia, and a tibial plate 6 borne by the tibial rod 5.

The femoral part 4 comprises a femoral rod 7 for inserting and fixing into the patient's femur and two concave condyles 8, 9 separated by a space.

The coupling part 3 comprises a first tibial insert 11, a second tibial insert 12 and a coupling means 13.

The first tibial insert 11, made e.g. of polyethylene, is disposed on the tibial plate 6 so as to be freely rotatable relative to a first axis of rotation 14 substantially parallel to the longitudinal axis of the tibial rod 5 and slightly offset towards the anterior side of the knee, relative to the tibial rod 5. The top part of the first or rotary insert 11 has two cavities with outer surfaces which are congruent with and correspond to the outer surfaces of the condyles 8, 9.

The second tibial insert 12, likewise made e.g. of polyethylene, is fixed to the tibial plate 6, a male projection 17 of the tibial plate being inserted into a female cavity formed in the bottom part of the fixed insert 12 so as to fix the insert 12 to the tibial plate 6. In addition a screw 18 screws the insert to the male projection 27.

Figure 3:
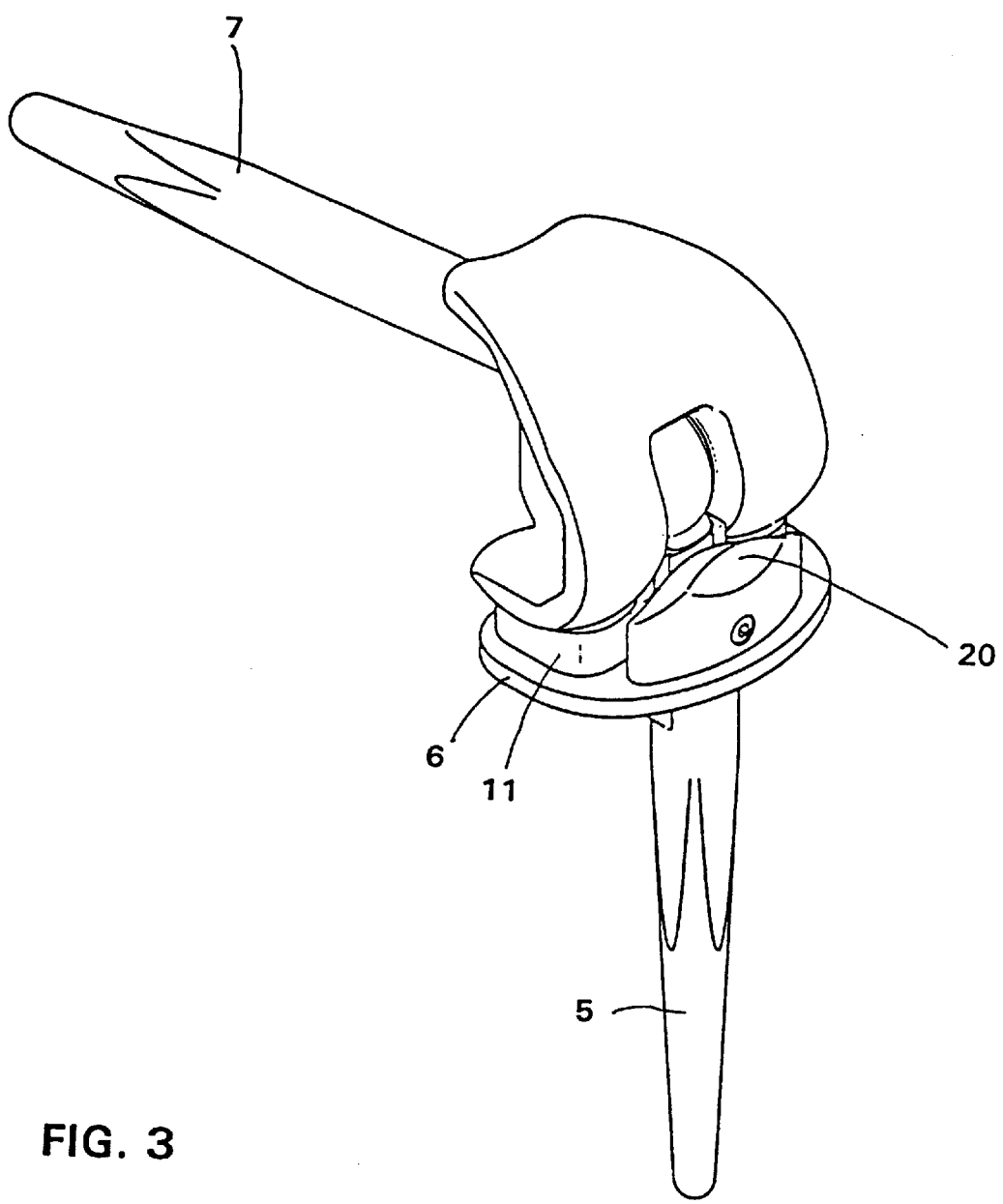
FIG. 3 is a perspective view of the prosthesis in FIG. 2 in the bent position.

The fixed insert 12 is shown more clearly in FIGS. 4a, 4b and 4c. On its top surface it has a ridge 19 dividing the upper surface into two upper surfaces 20, 21 sloping in opposite directions downwards. The ridge 19 has three portions 22, 23, 24 substantially in the form of arcs of a circle and with alternating convexity. The convexity of the middle portion 23 is upwards whereas the two side portions 22, 24 of the ridge have downwardly facing convexity (in the drawing). The upper surface 21 facing the movable insert 11 has a symmetrical curved shape relative to the plane of the tibial and femoral rods 5, 7 in FIG. 3, so as to form two sliding surfaces for the sliding surfaces of the condyles.

The coupling means 13 comprises a journal 27 which is fixed in rotation, e.g. via a hexagonal cross-section (not shown in the drawings) which co-operates with the correspondingly cross-sectional sides of a recess in the tibial rod 6. Alternatively the coupling means is rotatable in an e.g. circular cylindrical recess in the said tibial rod 6. The journal 27 extends through the rotary insert via a central opening in the rotary insert 11, so that the journal 27 forms the axis of rotation of the rotary insert 11.

The coupling means 13 also has a coupling head 25 which extends into the intercondylar space. The coupling head 25 has a recess 26 for receiving a coupling shaft 28 fixed to the condyles 8, 9 on either side of the intercondylar space. The coupling shaft transversely perpendicular to the axis of rotation of the rotary insert 11 and, if required, of the journal 27, is perpendicular to the antero-posterior axis.

The outer surface of the coupling shaft 28, in the part in the coupling head, is spherical and co-operates with a spherical part of the recess in the coupling head.

The femoral part 4, when bending relative to the tibial part 2, pivots around the coupling shaft 28, so as to move from a position where the knee is extended (femur and tibia substantially parallel, $\alpha=0$) to a position where the knee is bent to the maximum extent (femur and tibia at an angle $\alpha \approx 120°$).

In the extended position, the outer surfaces of the condyles 8, 9 abut the ridge 19 of the fixed insert and are thus prevented from rotating and bending, since bending is brought to a stop, and are also prevented from axial rotation since the concave outer surfaces of the two condyles 8, 9 at the front of the knee receive between them the ridge portion of the fixed insert 12 and abut the parts of the ridge during their movement in axial rotation.

As the knee bends, the outer surfaces of the condyles 8, 9 at the front of the knee no longer co-operate with the ridge 19 and the outer surface 21, so that a progressive clearance occurs between each condyle and its respective part of the outer surface 21. Consequently the femur can progressively move in axial rotation again. The shape of the condyles and of the ridge on the fixed insert are such that axial rotation of the femur is not entirely free except beyond a certain bending angle, e.g. 30° in the present case. Before the bending angle is reached, axial rotation is limited to a range determined by the respective shapes of the ridge and of the outer surface 21, e.g. in the present case ±10° for $\alpha_0 = 30°$.

The angle $\alpha$ is defined as the angle formed between the longitudinal axis of the femur and that of the tibia, $\alpha$ being variable from 0 (femur and tibia parallel, knee extended) to 120° (maximum angle of bending of the knee).

What we claim is:

1. A knee endoprosthesis comprising:
a tibial part comprising a tibial rod bearing a tibial plate,
a first tibial insert disposed on the tibial plate,
a femoral part comprising a femoral rod bearing two condyles each having a first sliding surface co-operating and congruent with a respective second sliding surface formed on the first tibial insert,
a coupling means for coupling the tibial part to the femoral part so that the femur can bend relative to the tibia from a position ($\alpha \approx 0$) where the knee is extended to a position ($\alpha_{max}$) where the knee is bent and vice-versa, and
a second tibial insert fixed to the tibial plate and having a shape such that when the knee is in the extended position the second fixed tibial insert projects into an intercondylar space formed between the condyles and fits into the seat formed by the intercondylar space so as to block any axial rotation of the femur relative to the tibia, and such that when the knee bends and the second insert comes out of its seat, a clearance between the walls of the intercondylar space and the second insert occurs progressively up to a bending angle ($\alpha_0$) determined in advance, after which the movements in axial rotation are free.

2. An endoprosthesis according to claim 1, wherein the second tibial insert has an upper surface comprising a ridge and an outer surface, and the shape of the condyles on the front of the knee are such that when the knee is in the extended position the ridge blocks any bending or proper rotation of the femur whereas as the knee bends a progressive clearance occurs between the condyles and the ridge and outer surface, permitting limited proper rotation up to a bending angle determined in advance and complete freedom beyond the bending angle determined in advance.

3. An endoprosthesis according to claim 1 wherein the first insert is mounted so as to be rotary relative to the tibial plate and the second insert is mounted so as to be fixed relative to the tibial plate.

4. An endoprosthesis according to claim 1 to 3, wherein the angle $\alpha_0$ determined in advance is between 20 and 40°.

5. An endoprosthesis according to claim 2 wherein the ridge or the insert comprises three portions in the form of arcs of a circle and having alternate convexity, the middle portion having upward-turned convexity so that it can extend into the intercondylar space, and the upper surface facing the movable insert is curved so as to form two second sliding surfaces respectively for the first outer sliding surfaces on the condyles.

6. An endoprosthesis according to claim 1 wherein the coupling means comprises a journal and a coupling head, the journal being mounted so as to be fixed in rotation or rotary in the tibial rod and extending through the first insert via an opening therein, the coupling head being recessed so as to receive a coupling shaft fixed to the condyles and enabling the femur to bend by rotating relative to the tibia.

7. An endoprosthesis according to claim 4, wherein $\alpha_0$ is about 30°.

* * * * *